United States Patent [19]

Lintilhac et al.

[11] 4,456,683

[45] Jun. 26, 1984

[54] STERILIZABLE TISSUE SQUEEZING DEVICE AND METHOD

[76] Inventors: Philip M. Lintilhac, Lakeview Ter., Waterbury Center, Vt. 05677; Thompson B. Vesecky, 20 Booth St., Burlington, Vt. 05401

[21] Appl. No.: 445,422

[22] Filed: Nov. 30, 1982

[51] Int. Cl.³ .................. C12Q 3/00; C12M 1/36; C12M 3/00; C12N 5/00
[52] U.S. Cl. ...................................... 435/3; 435/240; 435/241; 435/284; 435/285; 435/286; 435/289
[58] Field of Search .................. 435/3, 284, 285, 286, 435/289, 240, 241

[56] References Cited

U.S. PATENT DOCUMENTS 4,065,359 12/1977 Hurni ................................. 435/284

Primary Examiner—Robert J. Warden
Attorney, Agent, or Firm—Brumbaugh, Graves, Donohue & Raymond

[57] ABSTRACT

A sterilizable tissue squeezer is disclosed, comprising a forcing frame fixed to selectively vertically displaceable relative to the lid of a sterile culture vessel. The forcing frame has at its lower end a pair of tissue interface members which may be gradually and accurately adjusted toward and away from each other to provide a direct mechanical force to living tissue growing in sterile culture for manipulating the plane of cell division therein to afford possible control of the emergence of form and promote establishment of stems and roots in culture.

10 Claims, 2 Drawing Figures

STERILIZABLE TISSUE SQUEEZING DEVICE AND METHOD

BACKGROUND OF THE INVENTION

The present invention relates to a device for applying delicate, controlled mechanical forces to living tissue, and more particularly, to tissues growing in culture so as to control the plane of cell division therein.

It is possible to remove cells from a plant using known aseptic techniques, and to provide the cells so removed with an artificial nutritional environment which meets their maintenance and growth requirements. Unfortunately, in removing these cells from their parent plant, the cells are removed from their natural mechanical environment which comprises subtle but coherent pressures of surrounding tissues.

Previously, control over the development of tissues growing in sterile culture has been achieved through chemical, nutritional or hormonal means. However, manipulation of the chemical, nutritional or hormonal environment cannot compensate for the lost mechanical environment mentioned above. Because plant tissues differ widely in their ability to reestablish this mechanical environment, some varieties are to generate the local conditions necessary for the initiation of true stems and roots in culture, whereas other varieties are not. While considerable time, effort and money have been expended on some more hopeful varieties, e.g., Biloxi soy-bean and Sugar maple, in attempts to control their behavior in cell culture, many others are considered hopeless, among them many woody plants, because they produce only disorganized masses of random cells in cultures.

SUMMARY OF THE INVENTION

It is, therefore, an object of the present invention to provide a device for manipulating the plane of cell division so that otherwise randomly dividing cells may be organized into a coherent pattern, thereby affording the possible control of the emergence of form and the establishment of stems and roots in culture.

Another object of the present invention is to provide a device for the application of delicate, controlled mechanical forces to living tissue growing in a sterile culture, to control for the first time the developing form of the growing tissue by controlling the actual plane of cell division.

These and other objects, as will become apparent, are accomplished in accordance with the present invention by a device which, through the application of delicate and controlled direct mechanical forces, orients new partitions across cells at specific locations in a tissue, rather than by relying on the permeation of diffusable substances which, by nature, must act in a statistical way on the tissue at hand, inducing similar changes in all cells of similar competency as in methods heretofore known and used.

In accordance with the invention, the device comprises a forcing frame fixed to and depending downwardly from the lid of a sterile culture vessel. The vertical position of the frame within the vessel may be adjusted from outside of the vessel. The frame comprises a header block having two downwardly directed pairs of shims fixed at its opposite ends. On both the top and the bottom of the dual shims there are located shim gripper/spacer block arrangements. Between the lower pair of shim grippers and spacer blocks at the bottom of the dual shims there is provided a metallic bellows having TEFLON sandwiches at each end thereof which hold a pair of metal shims (such as leaf springs), which in turn have affixed at their ends TEFLON tissue interface members.

The leaf spring shims each have a pair of strain gauges thereon which act as force transducers. The strain gauges provide a signal indicative of the force being applied to the tissue by the tissue interface members. This signal is compared with a preset value and the resulting signal from the comparison circuit is used to drive a stepping motor, and thereby a peristaltic pump, in the appropriate direction to eliminate the discrepancy between the force actually transmitted and the desired, preset force.

The bellows are connected with the pump via fine air hoses which lead into the header block of the frame, and out of the header block via a main air hose connection.

BRIEF DESCRIPTION OF THE DRAWINGS

These and other features of the present invention, the scope of which will be pointed out in the appended claims, will be better understood by reference to the following detailed description of an exemplary embodiment, taken in conjunction with the attached Figures, in which:

DESCRIPTION OF EXEMPLARY EMBODIMENT

Figure 1:
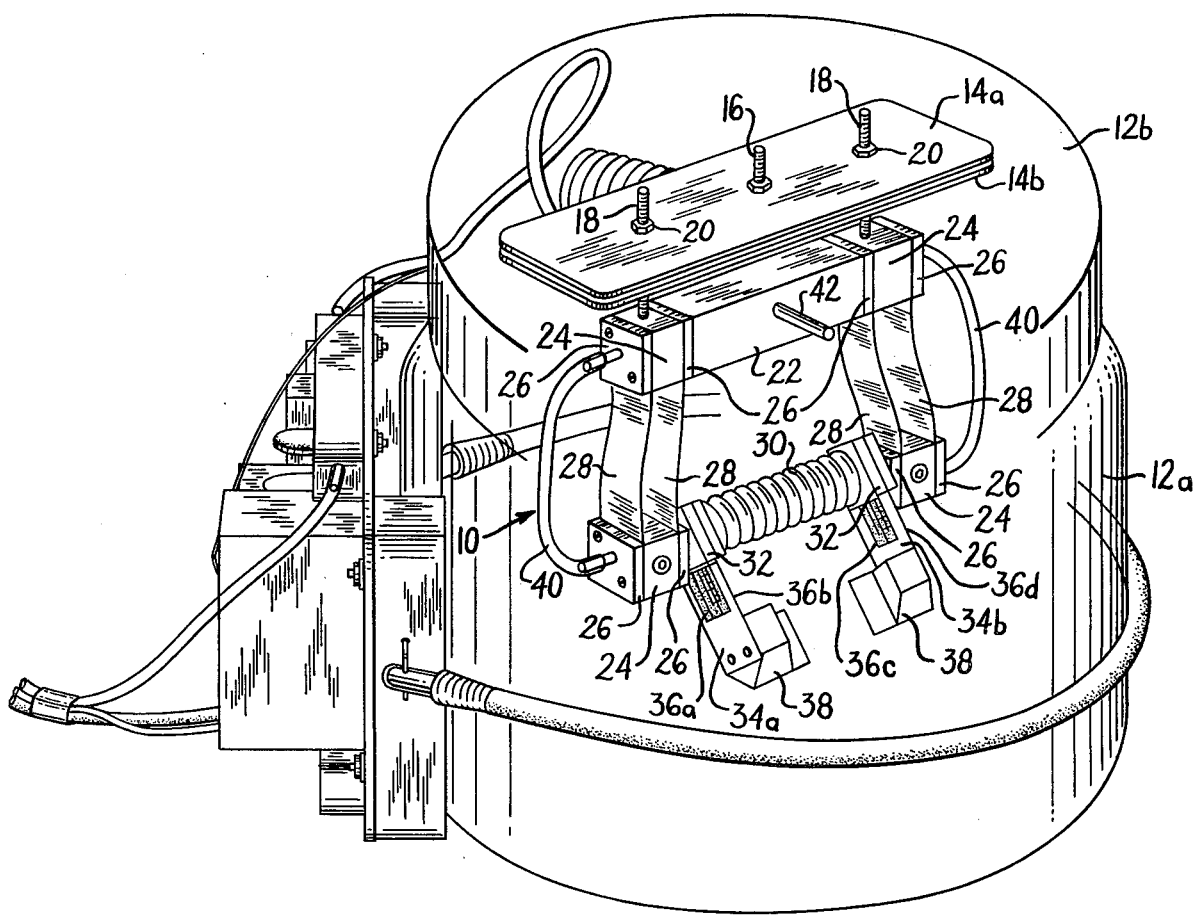
FIG. 1 is a schematic perspective view of a closed culture vessel illustrating the forcing-frame in its operative position depending downwardly from the culture vessel lid.

With reference to FIG. 1, the device according to the invention comprises a mechanical forcing frame 10, which will be described more fully below, housed within a sterile culture jar comprising a vessel 12a and a lid 12b. The frame 10 is attached to the lid 12b by two stainless steel plates 14a and 14b disposed on either side of the lid 12b and thus forming a sandwich. A centrally-disposed screw and nut 16 are used to adjust the tension of the stainless steel sandwich 14a and 14b on the lid 12b. Adjacent to the tension-adjusting screw and nut 16, are located two vertical adjustment screws 18 and cooperating nuts 20. By suitably adjusting the vertical adjustment screws 18 and nuts 20, the frame 10 may be raised and lowered within the culture vessel 12a relative to the lid 12b.

The mechanical forcing frame 10 comprises a TEFLON header block (or manifold) 22 having located at each end thereof stainless steel spacer blocks 24, to which the vertical adjustment screws 18 are connected. On each side of both stainless steel spacer blocks 24 there are arranged stainless steel shim grippers 26 which secure between themselves and the spacer blocks 24 downwardly depending dual shims 28. The lower ends of the dual shims 28 are fixed between pairs of shim grippers 26 and spacer blocks 24 in a manner similar to their upper ends.

Interposed between the lower shim gripper/spacer block pairs 24,26 of the frame 10 there is provided a metallic bellows 30 having TEFLON sandwich members 32 located at the opposite ends thereof. Extending from both of these TEFLON sandwich members 32 are oppositely oriented instrumental shims 34a, 34b (such as leaf springs), each of which carries a pair of strain gauges 36. (Strain gauges 36a and 36b, labelled but not shown) are located on the outside face and inside face, respectively, of shim 34a, and strain gauges 36c (and 36d labelled but not shown) are located on the inside face and outside face, respectively, of shim 34b. The strain gauges 36 operate as force transducers to provide a continuous measurement of the force being transmitted to the tissue which is gripped between the TEFLON tissue interface members 38 located at the ends of the two instrumental shims 34, as will be described below.

The bellows 30 is connected by fine flexible air hoses 40 to the TEFLON header block 22, and thence via a main air hose (not illustrated in FIG. 1) connected at one end to the main air connection 42 and at the other end to a pump (not illustrated in FIG. 1).

The pump comprises a low capacity peristaltic pump head driven by a reversible stepping motor, these being known. The peristaltic pump is virtually instantly reversible, valveless and relatively insensitive to small leaks since it can continue to pump against them. Further, there is no back-flow through the pump itself. Thus, there is provided an arrangement whereby extremely small pressure changes may be transmitted to the metal bellows 30, causing the frame 10, and thus the TEFLON interface members 38, to expand or contract away from or toward each other, respectively, very gradually, so that movement of the interface members are barely detectable by the naked eye. The actual speed that the interface members move is dependent upon the amount of difference between the actual and desired force values. Preferably, the movement should be as fast as possible, but still be slow enough so that tissue damage and excessive overshoot from a control standpoint is substantially avoided.

Figure 2:
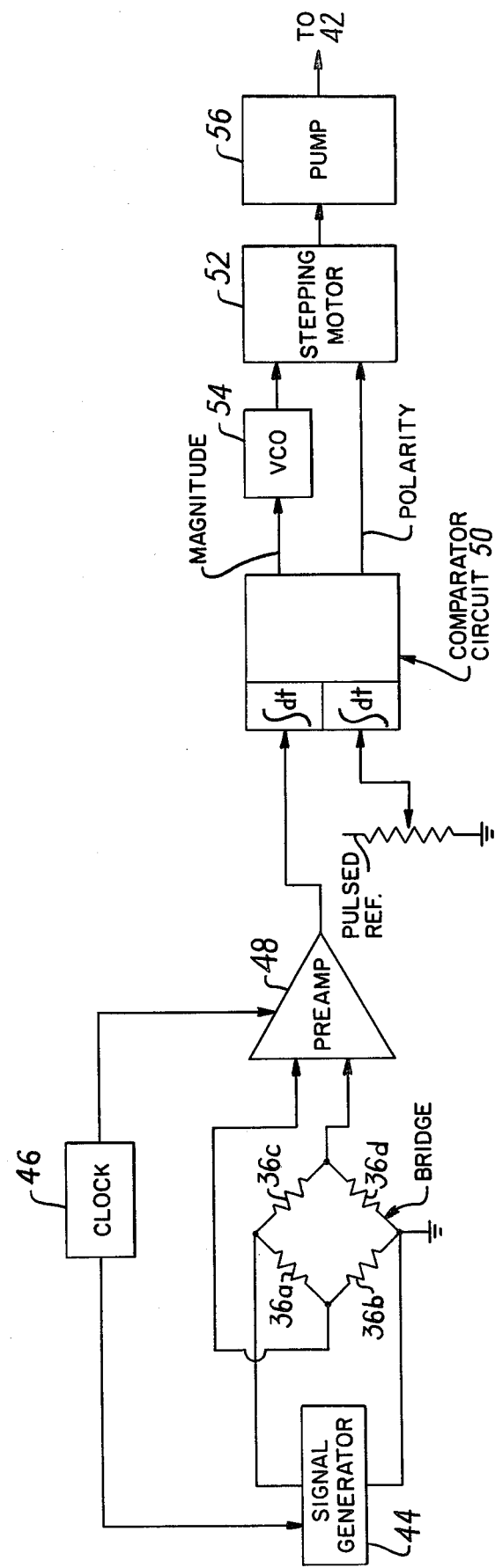
FIG. 2 is an electrical schematic of the circuit for measuring and controlling the force at the tissue interface member.

The strain gauges 36 provide a continuous measurement of the force transmitted to the tissue by the interface members 38. As shown in FIG. 2, these strain gauges 36 form a bridge circuit which becomes unbalanced as their resistance changes under load. A signal generator 44 receives a clock signal of about 1 Kilohertz from clock 46 and outputs an excitation signal having a frequency of about 1 Kilohertz to the bridge circuit. The excitation signal has a square waveform with a duty cycle or on-off ratio of 1:7 in order to minimize any overheating of the gauges 36. When the bridge circuit is unbalanced, an output is produced by the bridge during the "on" portion of the duty cycle, and this output is provided to preamplifier 48. The preamplifier 48 amplifies the output from the bridge and provides this amplified pulsed signal to comparator circuit 50.

The comparator circuit 50 receives both the amplified pulsed output signal from the bridge and a pulsed reference signal as inputs. The amplitude of the pulsed output signal is proportional to the amount of force actually applied by the tissue interface member, while the amplitude of the pulsed reference signal is proportional to the desired amount of force to be exerted by the tissue interface member. Means are provided to adjust the voltage level of the reference signal so that the desired amount of force to be exerted by the tissue interface members can be adjusted. These two signals are separately integrated to provide an actual D.C. signal and a reference D.C. signal, respectively, which are compared with each other.

The comparator provides two outputs; one output is a D.C. voltage signal whose magnitude is dependent on the difference between the actual and reference D.C. signals, and the other output is a polarity signal which provides an indication of whether the difference or amount of error, if any, between the active and reference signals is positive or negative, i.e. whether the actual force applied is respectively greater than or less than the desired force. The polarity signal is fed directly to the increase/decrease input of a stepping motor 52, while the D.C. output signal is provided to a voltage controlled oscillator (VCO) 54 which provides pulses to the stepping motor 52 at a frequency dependent upon the magnitude of the D.C. output signal.

The stepping motor responds to these signals to either increase or decrease the pressure provided by pump 56, depending upon whether the actual force exerted by the tissue interface members is respectively less than or greater than the desired force. Thus, the applied level of stress is adjusted to the preset stress level in an extremely smooth manner and over extended periods of time in a sterile environment.

Among the advantages of the present invention is the ability to maintain accurately milligram stress levels over the extended periods of time necessary for such tissue culture experiments. Also, this reliable operation in the milligram-range stress level is enhanced by the elimination of all sliding friction forces inasmuch as the bellows-actuated movement of the interface members 38 is accomplished by the bending motion of the dual shims 28.

The frame 10 itself requires little maintenance because there is no hydraulic fluid to complicate or contaminate the system. Also, because the bellows 30 and the connecting tubing are sealed and form a closed system with the pump, no air is exhausted or taken into the culture vessel. Furthermore, because the frame assembly is completely supported from the lid 12b, it may be positioned accurately with respect to the tissue explant located in the culture vessel without opening the vessel.

From the foregoing, it will be observed that numerous variations and modifications may be effected without departing from the true spirit and scope of the novel concept of the invention. It should be understood that no limitation with respect to the specific apparatus illustrated herein is intended or should be inferred. It is intended that the appended claims cover all such modifications that fall within the scope of the claims.

We claim:

1. A method of selectively applying direct mechanical force to living tissue in a sterile culture whereby the plane of cell division of said tissue is manipulated, comprising the steps of:
   (a) selecting a preset level of force to be applied to said tissue;
   (b) exerting a direct mechanical force on said tissue;
   (c) producing a signal indicative of said direct force;
   (d) comparing a signal indicative of said preset level of force with said signal indicative of said direct force and determining any discrepancy therebetween;
   (e) generating a signal which corresponds to said discrepancy to adjust said direct mechanical forces to said preset level of force; and thereafter repeating continuously steps b–e above, whereby said actual direct mechanical force applied to said living tissue continuously substantially approximates said preset level of force.

2. A tissue squeezing device comprising
a forcing frame means including tissue interface members, and
a bellows assembly means provided on said forcing frame means and including means for selectively moving said tissue interface members toward and away from each other to apply direct mechanical force to living tissue in sterile culture located between said tissue interface members, whereby new walls generated by active cell division are aligned with the force applied to said tissue through natural cellular regulatory process.

3. The tissue squeezing device according to claim 2, and further comprising
a means for generating a preset level of force to be applied to said living tissue,
a means for measuring the force actually applied to said living tissue and generating a measurement signal indicative thereof, and
a means for comparing said preset level and said actual level of force.

4. The tissue squeezing device according to claim 3, wherein said means for comparing generates an error signal, said error signal being used to activate control means for actuating said bellows assembly means to change the value of said actual force towards the value of said preset level of force.

5. The tissue squeezing device according to claim 4, wherein said forcing frame means further comprises a pair of instrumental shims depending therefrom, said tissue interface members being provided on said instrumental shims, each of said instrumental shims including a pair of transducer means operatively associated with said bellows assembly means and generating said signal indicative of the actual force applied to said living tissue.

6. The tissue squeezing device according to claim 5, wherein said tissue interface means are displaceable toward and away from each other by operation of a bellows means operatively disposed between said instrumental shims.

7. The tissue squeezing device according to claim 6, wherein said forcing frame comprises a header block having downwardly depending dual shims at each end thereof, said bellows means being arranged between the bottoms of said downwardly depending dual shims.

8. The tissue squeezing device according to claim 7, wherein said control means further comprises a stepping motor means, a pump means, and a circuit means which includes a comparison means, said measurement signal being compared by said comparison means with said preset force, wherein said error signal indicative of a discrepancy between said transducer signal and said preset force is generated by said comparison means, said comparison means-generated error signal being transformed into a pulse train and fed to said stepping motor, and wherein said motor drives said pump in the appropriate direction to eliminate said discrepancy.

9. The tissue squeezing device according to claim 8, wherein said pump is a peristaltic pump connected via a main air hose to a main air connection in said manifold, said manifold having further air hose connections to said bellows means.

10. The tissue squeezing device according to claim 9, wherein said instrumental shims to which said tissue interface means are connected comprise leaf springs.

* * * * *